United States Patent
Devore et al.

(10) Patent No.: US 9,289,396 B2
(45) Date of Patent: Mar. 22, 2016

(54) COLLAGEN-BASED IMPLANTS FOR SUSTAINED DELIVERY OF DRUGS

(75) Inventors: Dale P. Devore, Chelmsford, MA (US); Bruce H. Dewoolfson, Vienna, VA (US); Eliot Lazar, Orchard Park, NY (US)

(73) Assignee: Euclid Systems Corporation, Herndon, VA (US)

( * ) Notice: Subject to any disclaimer, the term of this patent is extended or adjusted under 35 U.S.C. 154(b) by 352 days.

(21) Appl. No.: 13/813,557

(22) PCT Filed: Aug. 1, 2011

(86) PCT No.: PCT/US2011/046098
§ 371 (c)(1), (2), (4) Date: Jan. 31, 2013

(87) PCT Pub. No.: WO2012/018715
PCT Pub. Date: Feb. 9, 2012

(65) Prior Publication Data
US 2013/0129807 A1    May 23, 2013

Related U.S. Application Data

(60) Provisional application No. 61/369,996, filed on Aug. 2, 2010.

(51) Int. Cl.
*A61K 9/06* (2006.01)
*A61K 9/70* (2006.01)
*A61K 47/42* (2006.01)
*A61K 9/00* (2006.01)
*A61K 47/46* (2006.01)
*A61K 31/5575* (2006.01)

(52) U.S. Cl.
CPC .............. *A61K 9/7007* (2013.01); *A61K 9/0024* (2013.01); *A61K 9/0051* (2013.01); *A61K 9/06* (2013.01); *A61K 31/5575* (2013.01); *A61K 47/42* (2013.01); *A61K 47/46* (2013.01)

(58) Field of Classification Search
CPC ...... A61K 9/06; A61K 47/46; A61K 31/5575
See application file for complete search history.

(56) References Cited

U.S. PATENT DOCUMENTS

| | | | | |
|---|---|---|---|---|
| 5,219,895 A | * | 6/1993 | Kelman | ................. C09J 189/06 522/68 |
| 5,259,998 A | * | 11/1993 | Reich et al. | ..................... 264/1.1 |
| 5,874,537 A | | 2/1999 | Kelman et al. | |
| 6,261,547 B1 | * | 7/2001 | Bawa et al. | ................. 424/78.04 |
| 2009/0280158 A1 | | 11/2009 | Butuner et al. | |

OTHER PUBLICATIONS

International Search Report from the US Patent Office for International Application No. PCT/US2011/046098, mailed Jan. 10, 2012.

* cited by examiner

*Primary Examiner* — Ali Soroush
(74) *Attorney, Agent, or Firm* — Finnegan, Henderson, Farabow, Garrett & Dunner LLP (57) ABSTRACT

The disclosure provides collagen-based constructs for use in drug delivery.

17 Claims, 3 Drawing Sheets

Release from non-pretreated Latanoprost Wafers

FIG 3

Release from pretreated Latanoprost Wafers

COLLAGEN-BASED IMPLANTS FOR SUSTAINED DELIVERY OF DRUGS

RELATED APPLICATIONS

This application claims benefit of U.S. Provisional Application No. 61/369,996, filed Aug. 2, 2010, the disclosure of which is incorporated by reference in its entirety.

FIELD OF THE INVENTION

The present invention describes collagen-based constructs for sustained delivery of agents and drugs to a localized site of interest.

BACKGROUND

Oral or injectable drugs are commonly used to treat various diseases and conditions. However, these therapeutic approaches result in systemic drug exposure that may be unnecessary or even undesirable. Further, most orally-administered drugs require at least daily dosing to maintain adequate drug levels. Even when targeted drug delivery is possible because of the accessible location of the tissue to be treated, it is still often difficult to attain adequate drug levels over an extended period of time for various reasons. Some of these difficulties are illustrated by treatments targeted to the eyes, ears, and nasal sinuses.

Ocular Tissues

The treatment of many ophthalmic diseases and post-operative conditions require frequent administration of drugs to the ocular tissues. Many medications must be applied topically to the eye and one common form of treatment is the use of drops or ointments. The topical formulation is administered by the patient or caregiver using an eye dropper or dispenser. However, a substantial disadvantage of this method of drug delivery is that the medication rapidly drains from the ocular surface into the lacrimal system through an opening in the eyelid called the punctum. Furthermore, the medication is rapidly diluted by the tears secreted by the lacrimal gland. This problem is further compounded by the patients themselves: one of the principal limitations of topical medication is poor patient compliance. The more often a patient is required to use medication, the less likely they will administer the proper dose at the proper time.

Thus, topical treatments do not provide a continuous, prolonged delivery of medication and the exact dosage achieved at the target tissue is unpredictable. Intermittent administration also is problematic because there is an initial overdosage followed by a rapid decrease in concentration due to dilution and lacrimal drainage to ineffective levels.

Another approach for achieving localized drug delivery involves the injection of drug directly under the conjunctiva or tenon's capsule, intra-camerally or intra-vitreally. Unfortunately, this approach may require periodic injections of drug to maintain an effective drug concentration at the target site and has many potential adverse effects.

Accordingly, there is a need for a sustained, controlled, delivery system for ophthalmic drugs.

Otic Tissues

Similar to ocular liquid treatments, the delivery of therapeutic agents in a controlled and effective manner to inner ear tissues is difficult, particularly when considering the tissue structures of the inner ear (e.g. those portions of the ear surrounded by the otic capsule bone and contained within the temporal bone which is the most dense bone tissue in the entire human body). The same delivery issues exist in connection with tissues leading into the inner ear (e.g. the round window membrane).

Conventional methods for delivery of therapeutic agents to the inner ear involve filling the middle ear with a solution or other carrier of the therapeutic agent. Although these methods may ultimately result in delivery of drug into the inner ear (e.g., by perfusion through the round window membrane), delivery of the therapeutic agent is generally not well controlled and/or use of the carrier materials may be associated with adverse side effects.

Thus, there is also a need for a sustained, controlled delivery system for otic agents.

Sinus (Nasal) Tissues

Similar to ocular and otic liquid treatments, there are issues regarding nasal treatments. Treatments for sinusitis include systemic antibiotics, but systemic administration of antibiotics, particularly over extended periods as may be required to treat sinusitis, can have undesirable effects on the flora of the digestive tract and reproductive system. Intranasal corticosteroid sprays and intranasal decongestant sprays and drops have also been used. However, the use of intranasal sprays and drops by most patients does not result in the drug actually entering the affected intranasal sinuses. Rather, such sprays and drops typically contact only tissues located within the nasal cavity.

Therefore, there is also a need for a sustained, controlled delivery systems for sinus (nasal) agents.

Drug Delivery Systems

Various methods have been developed to prolong drug exposure following a single dosing. For example, the drug may be formulated into a slow release formulation (see, for example, Langer (1998) NATURE 392, Supp. 5-10). In some of these systems the drug is conjugated with polymers that are degraded, for example, by proteolytic enzymes or by hydrolysis, to gradually release drug into the target site following administration. In another approach, drug is trapped throughout an insoluble matrix. Following administration, drug then is released via diffusion out of, or via erosion of, the matrix. Alternatively, drug can be encapsulated within a semi-permeable membrane or liposome. Following administration, the drug is released either by diffusion through the membrane or via breakdown of the membrane.

Specialized deliver systems for the eye, ear, and nasal sinuses have also been developed, and some of these are described below.

Ocular Delivery Systems

Several systems shown in U.S. patents describe large ocular inserts to continuously deliver active agents to the eye. Certain inserts disperse the drug and require removal of the carrier of the drug once the drug has been delivered. However, U.S. Pat. Nos. 3,845,201; 4,164,559 and 4,179,497 show various inserts in the form of large pellets which dispense drug over a period of time and eventually are completely eroded, and thus do not require removal after drug delivery.

U.S. Pat. No. 4,164,559 describes an ophthalmic drug delivery system comprising (a) an enzyme-extracted, chemically-modified collagen thin membrane carrier selected from the group consisting of esterified collagen and acylated collagen and having a pH in the range of 5.5-9.0 whereby the carrier is soluble in the tear fluid under physiologic conditions, and (b) an ophthalmically active drug incorporated into the carrier. U.S. Pat. No. 4,882,150 describes an ophthalmic drug delivery system, which includes at least one particle of bioerodible material, and a liquid or ointment carrier which includes ophthalmic drug to be delivered to the ocular area. The bioerodible material includes collagen. U.S. Pat. No.

5,512,301 describes collagen-containing sponges comprising an absorbable gelatin sponge, collagen, and an active ingredient and the use of the sponges in methods of enhancing wound healing of external and internal wounds. U.S. Pat. Nos. 6,197,934 and 6,448,378 describes collagen films which rapidly dissolve at 35° C., methods for preparing the collagen films, and their use for delivering a dose of therapeutic compound to a specific tissue site. U.S. Pat. No. 5,418,222 describes a multi-layered collagen film for use in controlled release of an active ingredient, said film comprising one or two rate controlling layers and one or more drug reservoir layers, said layers comprising non-fibrillar collagen and contacting each other in a stacked conformation such that a rate controlling layer is situated at one or both ends of the stack and contacts only one other layer, said other layer being a drug reservoir layer.

These inserts have certain advantages over liquid treatments in that a more predictable dosage is obtained because drug is continuously dispensed over a period of time without rapid washout. Thus, the unit ocular inserts provide predictable dosage over a period of time without the requirement of repeated applications as required with liquid treatments. However, the inserts described in these patents are reported to support drug release only over a period of time ranging from less than a day to about a week.

Various ocular drug delivery implants have also been described in an effort to improve and prolong drug delivery. For example, U.S. Pat. No. 3,949,750 discloses a punctual plug made of a tissue-tolerable, readily sterilizable material, such as Teflon, HEMA, hydrophilic polymer, methyl methacrylate, silicone, stainless steel or other inert metal material. The punctual plug may be impregnated with ophthalmic medication or may contain a reservoir of the ophthalmic drug. U.S. Pat. No. 5,053,030 similarly discloses an intracanalicular implant. U.S. Pat. No. 5,469,867 discloses a method of blocking a channel, such as the lacrimal canaliculus by injecting a heated flowable polymer into the channel and allowing it to cool and solidify. The polymer may be combined with a biologically active substance that could leach out of the solid punctum once it has formed in the channel. WO 99/37260 discloses a punctual plug made of a moisture absorbing material, which is not soluble in water, such as a modified HEMA. An inflammation inhibitor, such as heparin, may be added to the material from which the punctual plug is made. U.S. Pat. No. 6,196,993 discloses a punctual plug containing glaucoma medication. The medication is contained in a reservoir within the plug that is in fluid communication with a pore through which the medication is released onto the eye. WO 2006/031658 discloses lacrimal canalicular inserts including a polymer component and a therapeutic component. Similarly, U.S. Pub. No. 2006/0020248 discloses an ophthalmological device for lacrimal insertion that includes a reservoir for a medication. U.S. Pub. No. 2004/0013704 discloses solid or semi-solid implant compositions lacking polymeric ingredients. These implant compositions are made of lipophilic compounds and may contain an ophthalmic drug. They may be implanted anywhere in the eye including the punctum or lacrimal canaliculous. U.S. Pub. No. 2005/0232972 discloses ocular implants to which active agents have been applied to at least one surface. In one embodiment, a porous or absorbent material can be used to make up the entire plug or implant which can be saturated with the active agent. WO 2004/066980 discloses a device for delivering a carbonic anhydrase inhibitor (CAI) to the eye over an extended period of time. In one embodiment, the device has an inner CAI-containing core and an outer polymeric layer. The outer layer may be permeable, semi-permeable, or impermeable to the drug. Where the outer layer is impermeable to the drug, it may have one or more openings to permit diffusion of the CAI. U.S. Pub. No. 2003/0143280 discloses the use of biodegradable polymer capsules for treating ophthalmic disorder including dry eye and glaucoma. The capsules are made of any biodegradable, biocompatible polymer and may contain a treating agent.

Otic Delivery Systems

Otic delivery systems that have been described use naturally-occurring materials such as gelatin (e.g., Gelfoam, see, e.g., Silverstein Ann Otol Rhinol Laryngol Suppl. 112:44-8. (1984); Lundman et al. Otolaryngol 112:524 (1992); Nedzelski et al. Am. J. Otol. 14:278-82 (1993); Silverstein et al. Ear Nose Throat J 75:468-88 (1996); Ramsay et al. Otolaryngol. 116:39 (1996); Ruan et al. Hear Res 114:169 (1997); Wanamaker et al. Am. J. Otology 19:170 (1998); Arriaga et al. Laryngoscope 108:1682-5 (1998); and Husmann et al. Hear Res 125:109 (1998)), hyaluronan or hyaluronic acid (see, e.g., WO 97/38698; Silverstein et al. Am J Otol. 19(2):196-201 (1998)), or fibrin glue or other fibrin-based vehicle (see, e.g., Balough et al. Otolaryngol. Head Neck Surg. 119:427-31 (1998); Park et al. Laryngoscope 107:1378-81 (1997)).

Although these methods may ultimately result in delivery of drug into the inner ear (e.g., by perfusion through the round window membrane), delivery of the therapeutic agent is generally not well controlled and/or use of the carrier materials may be associated with adverse side effects. For example, use of gelatin-based materials such as Gelfoam can cause fibrosis in the middle ear cavity (see, e.g., Laurent et al. Am. J. Otolaryngol 7(3):181-6 (1986); Liening et al. Otolaryngol. Head Neck Surg. 116:454-7 (1997)). Furthermore, naturally-occurring carrier materials generally do not retain their shape following introduction into the ear (e.g., the materials are naturally viscous or become more liquid upon introduction into the ear). The changes in the shape of the carrier materials make it extremely difficult to completely retrieve the materials from the site of introduction if such should be desired (e.g., to terminate therapy). It may even prevent delivery of additional therapeutic agents in subsequent treatments (see, e.g., Silverstein et al. Am J. Otol 18:586-9 (1997), describing how gelfoam becomes paste-like and prevents future injections of this material from reaching the inner ear fluids).

Sinus (Nasal) Delivery Systems

The introduction of drugs directly into the sinuses has been proposed by others, but has not become a widely used treatment technique. For example, U.S. Pub. 2004/0116958A1 (Gopferich et al.) describes a tubular sheath or "spacer" formed of biodegradable or non-biodegradable polymer that, prior to insertion in the patient's body, is loaded with a controlled amount of an active substance, such as a corticosteroid or anti-proliferative agent. Surgery is performed to create a fenestration in a frontal sinus and the sheath is inserted into the fenestration. In some embodiments, the sheath is formed of multiple layers of polymeric material, one or more of which is/are loaded with the active substance and one or more of which is/are free of the active substance. In other embodiments, the sheath has a "hollow body" which forms a reservoir system wherein the active substance is contained and a membrane which controls the release of the active substance from the reservoir.

Also, Min, Yang-Gi, et al., "Mucociliary Activity and Histopathology of Sinus Mucosa in Experimental Maxilary Sinusitis: A Comparison of Systemic Administration of Antibiotic and Antibiotic Delivery by Polylactic Acid Polymer," Laryngoscope, 105:835-842 (August 1995) describes experiments wherein experimental sinusitis was induced in three groups of rabbits by "pasting" the natural sinus ostia, forming an incision and small bore hole made in the anterior wall of the sinus, introducing pathogenic microbes through the bore hole and then closing the incision. Five days after introduction of the pathogenic microbes, the natural sinus ostia were reopened and the rabbits were divided into three (3) groups. Group 1 (control) received no treatment. Group 2 received repeated intramuscular injections of ampicillin. In the animals of Group 3, 1.5 cm×1.5 cm sheets of polylactic acid polymer (PLA) film containing ampicillin (0.326 mg/sheet) were rolled up and inserted through the natural ostia into the infected sinuses. Thereafter, measurements of mucocilliary transport speed were made and the tissues lining the affected sinuses were examined histopathologically. The authors concluded that the therapeutic effect observed in the animals that had received intrasinus implants of PLA/Ampicillin film (Group 3) was significantly better that that observed in the untreated control animals (Group 1) or those that has received repeated intramuscular doses of ampicillin (Group 2).

U.S. Pat. No. 3,948,254 (Zaffaroni), incorporated by reference, describes implantable drug delivery devices comprising a drug reservoir surrounded by a microporous wall. The reservoir may be formed of any of a variety of solid drug carriers that are permeable to passage of the drug. Zaffaroni describes a number of applications for the implantable drug delivery devices including placement in a nasal passage. That reference also discusses zero order release and how such release can be determined.

Other publications have also reported that introduction of drugs directly into the paranasal sinuses is effective in the treatment of sinusitis. See, Tarasov, D. I., et al., Vestn Otorinolaringol. Vol. 6, Pages 45-7 (1978). Also, R. Deutschmann, et al., Stomat. DDR 26 (1976), 585-592 describes the placement of a resorbable drug delivery depot within the maxillary sinus for the purposes of eluting drugs, specifically chloramphenicol. In this clinical series a water soluble gelatin was used as carrier that was mixed with the drug prior to application and introduced as a mass into the sinus. Since the substance had little mechanical integrity and dissolved in a relatively short timeframe, to achieve a therapeutic effect, the author suggested that it must be instilled every 2 to 3 days. U.S. Pat. No. 6,398,758 to Jacobsen et al. describes a hollow cylindrical sponge loaded with drug and pressed against a blood vessel wall. This allows the drug to contact the wall while sustaining blood flow within the center of the lumen. Further, a skin is provided to direct the drug into the walls of the blood vessel and prevent drug from flowing into the lumen. While sponges loaded with drug at the time of their application do permit some degree of sustained release, the time required to load them also correlates closely with the time over which they will elute substance. Thus, if delivery is required for a longer period of time additional mechanisms must be employed to regulate their release.

Many of the devices described above are reservoir-type drug-delivery devices that contain a receptacle or chamber for storing the drug. There are drawbacks to reservoir drug delivery devices in that they are difficult to manufacture, difficult to achieve drug content uniformity (i.e., device to device reproducibility, particularly with small ocular devices), and they carry the risk of a "dose dump" if they are punctured.

There are also several examples in the patent literature where various sustained release mechanisms have generally been proposed using systems with pre-incorporated drugs into matrices or polymers. These include U.S. Pat. No. 3,948, 254 (Zafferoni), US 2003/0185872A2 (Kochinke), WO 92/15286 (Shikani), and U.S. Pat. No. 5,512,055 (Domb, et al.). In general, these references discuss various materials and structures that may be used to construct sustained drug delivery vehicles and provide an overview of the state of sustained drug delivery art. None of these references, however, describes specific methods, means, or structures which would permit them to be easily adapted for the intended uses targeted in this application.

In matrix drug delivery devices the drug is dispersed throughout a polymeric matrix and is released as it dissolves or diffuses out of the matrix. Matrix devices have an advantage over reservoir devices in that they are not subject to a dose dump if punctured. A disadvantage of matrix devices is that it can be difficult to achieve zero-order drug release kinetics. Zero-order drug release or near zero-order drug release is desirable because the rate of drug release is independent of the initial concentration of the drug, thus the drug can be released at therapeutic levels over a sustained period of time. The manufacture of matrix devices can also present difficulties when the drug and the polymer are processed and extruded at elevated temperature and/or pressure as this may reduce the activity of the drug.

DeVore has previously described several collagen-based drug delivery systems, but those systems provided either rapid release of the therapeutic component or provided an initial bolus release of the therapeutic agent followed by a time declining release of the therapeutic agent. Such compositions did not provide desired zero order release, or involved in vivo polymerizing gels. For example, WO 00/47114 describes an injectable fibrillar collagen solution comprising bone morphogenic proteins that polymerizes in situ to form a matrix, but in this system 50% of the drug was released within the first 24 hours and the longest period of release measured was 400 hours. WO 00/47130 similarly describes collagen solutions that convert to gels following in vivo placement. The solutions may be used for delivering cells and or drugs to a tissue by crosslinking them to the collagen using ultraviolet radiation. When release of the drug acyclovir was tested in this in vivo polymerizing gel system, release was detected at the longest time point measured, 28 days. In an abstract (DeVore et al., Abstract 5126-B524, ARVO, 2006), propose the use of this system to deliver sustained release of growth factors and other agents for treatment of retinal disorders for up to 2 months, but no details were given. In ARVO abstract 480-B454 (*Invest Ophthalmol Vis Sci* 2005; 46:) release and diffusion of dexamethasone from collagen gels and films through human scleral tissue was measured for a 24 hour period. No long-term release was evaluated. In ARVO abstract 1816-D686 (*Invest Ophthalmol Vis Sci* 2008; 49: E-Abstract 1816) release of POT-4 (a strong complement inhibitor peptide) from collagen gel was bi-phasic with an initial burst followed by sustained release.

The collagen-based drug delivery constructs of the present invention address deficiencies in the art by providing matrices that achieve zero-order or near zero-order drug-release kinetics typically associated with reservoir devices, but without the risk of dose dumping and the manufacturing difficulties of reservoir devices. Further, while the collagen-based drug delivery constructs are illustrated in the context of ophthalmic, otic, and sinus drug delivery, those uses are illustrative only as the collagen-based drug delivery constructs can be used anywhere in the body that prolonged delivery of a precise dose of drug or other agent is needed.

SUMMARY OF INVENTION

The present application provides collagen-based constructs, such as film, wafer, or membrane-type delivery systems, for use in sustained and/or controlled release of an agent or drug. In one aspect, the film, wafer, or membrane is comprised of at least one layer composed of crosslinked, chemically derivatized collagen. The collagen may be chemically derivatized to change the net charge on collagen to enhance ionic binding of active agents or drugs and wherein said film or membrane delivery systems may be multi-layer in composition where at least one layer is a rate controlling layer composed of derivatized collagen on one surface of the film or membrane providing a barrier to diffusion of the active agent or drug.

In one embodiment, the collagen in the delivery construct is acylated to alter ionic charge and charge density and to provide a soluble collagen composition at neutral pH. In another embodiment, the collagen is altered to increase net negative charge by reacting the collagen solution with acylating agents selected from the group consisting of anhydrides including maleic anhydride, succinic anhydride, glutaric anhydride, citractonic anhydride, methyl succinic anhydride, itaconic anhydride, methyl glutaric anhydride, dimethyl glutaric anhydride, phthalic anhydride, and many other such anhydrides; acid chlorides including oxalyl chloride, malonyl chloride; sulfonyl chlorides including chlorosulfonylacetyl chloride, chlorosulfonylbenzoic acid, 4-chloro-3-(chlorosulfonyl)-5-nitrobenzoic acid, 3-(chlorosulfonyl)-P-anisic acid, and others; sulfonic acids including 3-sulfobenzoic acid and others.

In some embodiments, the concentration of acylating agent to chemically derivatize collagen is less than 5% (weight per weight collagen solids) to minimally increase net negative charge. Alternatively, the concentration of acylating agent to chemically derivatize collagen is less than 20% (weight per weight collagen solids) to moderately increase net negative charge. In still other embodiments, the concentration of acylating agent to chemically derivatize collagen is more than 25% (weight per weight collagen solids) to maximally increase net negative charge. In one embodiment, the collagen is altered to increase net positive charge by reacting the collagen solution with acylating agents selected from 4,6-diamino-2-methylthiopyrimidine-5-sulfonic acid. In still other embodiments, the concentration of acylating agent to chemically derivatize collagen is less than 5% (weight per weight collagen solids) to minimally increase net negative charge. And in yet other embodiments, the concentration of acylating agent to chemically derivatize collagen is less than 20% (weight per weight collagen solids) to moderately increase net negative charge. In still other embodiments, the concentration of acylating agent to chemically derivatize collagen is more than 25% (weight per weight collagen solids) to maximally increase net negative charge.

In yet another aspect, the invention provides a delivery system or collagen-based construct in which films, wafers, or membranes of acylated collagen containing extended therapeutic concentrations of selected drugs are exposed to ultraviolet irradiation in an oxygen-free (for example, a nitrogen) atmosphere for time periods ranging from about 2 minutes to about 20 minutes. In some embodiments the exposure is for time periods ranging from about 14 to about 19 minutes, about 15 to about 19 minute, about 16 to about 18 minutes, about 15, about 16, about 17, about 18, or about 19 minutes. In some embodiments, the exposure time is approximately 18 minutes. Thus, in some embodiments, the delivery system is exposed to ultraviolet irradiation in a nitrogen atmosphere to produce collagen films, wafers, or membranes with defined resorption characteristics such that the film, wafer, or membrane delivers therapeutically effective amounts of drug for a period of time of at least about 3 to 6 months.

In one aspect, the collagen constructs of the invention are used to deliver extended therapeutic concentrations of ophthalmic, otic, and sinus (nasal) drugs. Examples of such drugs are given in the Detailed Description. In some embodiments, the drugs or agents are those that have low water or aqueous solubility. Thus, in particular aspects, the collagen-based constructs comprise an ophthalmic, otic, or sinus (nasal) drug that has low water or aqueous liquid solubility.

One example of a drug with low water solubility that may be delivered using the collagen-based constructs of the invention is Latanoprost, which is commonly used in methods of treating glaucoma. In some embodiments, the collagen construct delivers an extended therapeutic concentration of Latanoprost that is at least about 150 µg per film, wafer, or membrane to provide an effective dosage of about 1.5 µg per day for at least about 90 days. In other embodiments, the extended therapeutic concentration of Latanoprost is at least about 300 µg per film, wafer, or membrane to provide an effective dosage of about 1.5 µg per day for at least about 180 days. In some embodiments, the delivery is sustained, zero-order delivery. In other embodiments, the delivery includes a bolus release at about day 1-3, followed by controlled delivery of a therapeutically effective amount of Latanoprost for at least about 6 months. In some embodiments, the delivery is for at least about 6 months but not for more than one year. Other delivery profiles and time periods are set forth in the Detailed Description and Examples.

In certain aspects, the delivery system comprises a collagen-based film, wafer, or membrane as described above that further comprises a layer which is a barrier to drug diffusion. In these embodiments, the films, wafers, or membranes provide essentially unidirectional delivery of the selected drug through the non-barrier layer or layers. In some embodiments, the barrier layer is composed of collagen acylated with chemical agents imparting chemical barriers to diffusion of selected drugs. Examples of acylating agents that may be used to produce the barrier layer are those agents producing biologically compatible collagenous reaction products comprising ethylenically unsaturated monomerically substituted collagen, the monomeric substituents being essentially free of nitrogen, e.g., methyacrylate, styrene, polyvinyl, ethylene.

In still another aspect, the invention provides a method for preparing a collagen-based, film or construct comprising a therapeutic drug and capable of providing sustained and/or controlled release of that drug, the method comprising:
  (i) preparing derivatized collagen;
  (ii) dissolving the derivatized collagen precipitates in physiological buffer at concentrations ranging from 10 mg/mL to 100 mg/mL;
  (iii) adding active drug in a concentration that provides sustained release at therapeutic levels for at least 3 to 6 months;
  (iv) optionally centrifuging the drug-containing, derivatized collagen to remove air bubbles;
  (v) casting the collagen-drug solution into a thin layer or onto a mold;
  (vi) drying or partially drying the solution to form a film, membrane, or wafer;
  (vii) exposing the film, membrane, or wafer to ultraviolet ("UV") radiation in an oxygen-free atmosphere, such as a nitrogen atmosphere, for from about 17 to about 19 minutes; and
  (viii) recovering the UV-crosslinked, drug-containing, film, membrane, or wafer.

In some embodiments, the concentration of the derivatized collagen in step (ii) is adjusted to a range between 15 and 100 mg/mL, between about 25 and about 60 mg/mL, or between about 30 and about 45 mg/mL.

In some embodiments, the ultraviolet radiation exposure in step (vii) is for about 18 minutes.

In some embodiments, the UV-crosslinked collagen construct is further treated by incubating it in a solution, for example a saline solution. In some embodiments, the solution treatment is for about 1 day, 2 days, 3 days, 4 days, 5 days, 6 days, 7, days, about 1 week, about 2 weeks, or about 3 weeks. In some embodiments the solution treatment results in collagen construct that releases drug with zero order kinetics or with near zero order kinetics. In still other embodiments, the solution treatment results in collagen-based construct that releases drug with an initial bolus until about day 1, day 2, or day 3, followed by controlled release for at least about 3, 4, 5, 6, 7, 8, 9, 10, 11, or 12 months. In still further embodiments, the controlled release is for at least 6 months, but not for more than about 7, 8, 9, 10, 11, or 12 months.

In some embodiments, the method includes partial drying of the solution and an additional step of applying a barrier layer comprising collagen derivatized by an acylation agent that imparts a barrier to diffusion of the drug to one side of the drug reservoir layer prior to ultraviolet radiation of the film or membrane.

Collagen-based film, wafers, or membrane prepared by the methods are of course part of the invention.

In one particular aspect, the invention provides a collagen-based film, wafer, or membrane delivery system for use in sustained and/or controlled release of an extended therapeutic concentration of Latanoprost, said film or membrane comprising at least about 150 μg of Latanoprost in one or more layers of glutaric anhydride-derivatized collagen, wherein the film or membrane has been crosslinked with ultraviolet radiation in a nitrogen atmosphere for from 17 to 19 minutes. In one specific embodiment, the film, wafer, or membrane provides controlled release of about 1.5 μg Latanoprost per day for at least about 90 days. In certain embodiments, therefore, the film, wafer, or membrane may be used in a method of treating glaucoma comprising administering to the eye of a glaucoma patient the collagen-based film, wafer, or membrane delivery system comprising Latanoprost.

In an alternate aspect, the invention provides a collagen-based, ultraviolet radiation crosslinked, film, wafer, or membrane construct comprising at least one layer of chemically derivatized collagen and an amount of an ophthalmic, otic, or nasal drug that has low water or aqueous solubility, wherein the amount of the drug is sufficient to provide a therapeutically effective amount of drug per day over a period of about six months, and further wherein the construct has been exposed to ultraviolet radiation crosslinking for a period of 17 to 19 minutes in a low oxygen environment. In one embodiment, the drug present in the film, wafer, or membrane is resistant to removal by a 1 day treatment in an aqueous buffer, while in another embodiment it is resistant to removal by a 7 day treatment in an aqueous buffer.

In certain embodiments, the film, wafer, or membrane further comprises a barrier layer of collagen derivatized by an acylation agent.

In still another aspect, the invention provides a collagen-based, ultraviolet radiation crosslinked, film, wafer, or membrane delivery system comprising at least one layer of glutaric anhydride-derivatized collagen and at least about 150 μg of Latanoprost, wherein the film, wafer, or membrane has been crosslinked with ultraviolet radiation for from 17 to 19 minutes. In some embodiments, the film, wafer, or membrane provides sustained and/or controlled release of about 1.5 μg Latanoprost per day for at least about 6 months but for less than one year. In other embodiments, the film, wafer, or membrane comprises at least about 300 μg Latanoprost to provide an effective dosage of about 1.5 μg per day for at least about 180 days of sustained and/or controlled delivery.

In this aspect as well, the collagen-based film, wafer, or membrane of may be one in which the Latanoprost present in the film, wafer, or membrane is resistant to removal by a 1 day treatment in an aqueous buffer. Likewise, the collagen-based film, wafer, or membrane may be one in which the Latanoprost present in the film, wafer, or membrane is resistant to removal by a 7 day treatment in an aqueous buffer.

In this aspect as well as any other aspects of the invention, the film, wafer, or membrane may further comprise a barrier layer of collagen derivatized by an acylation agent.

In yet another aspect, the invention provides a method for preparing a collagen-based film, wafer, or membrane construct comprising a therapeutic drug and capable of providing sustained and/or controlled release of that drug, the method comprising:

(i) preparing derivatized collagen;
(ii) dissolving the derivatized collagen precipitates in physiological buffer at concentrations ranging from 10 mg/mL to 100 mg/mL;
(iii) adding active drug in an amount and concentration sufficient to provide sustained release at therapeutic levels for at least 3 to 6 months;
(iv) optionally centrifuging the drug-containing, derivatized collagen to remove air bubbles;
(v) casting the collagen-drug solution into a thin layer or onto a mold;
(vi) drying or partially drying the solution to form a film, membrane, or wafer;
(vii) exposing the film, membrane, or wafer to ultraviolet ("UV") radiation in a low oxygen atmosphere for from about 17 to about 19 minutes; and
(viii) recovering the UV-crosslinked, drug-containing, film, membrane, or wafer.

In one embodiment, the ultraviolet radiation exposure in step (vii) is for about 18 minutes. In other embodiments, the method further comprises treating the UV-crosslinked collagen construct an aqueous solution for about 1, 2, 3, 4, 5, 6, or 7 days. In certain embodiments, the drug is Latanoprost in an amount sufficient to release an effective dosage of about 1.5 μg per day for at least about 180 days. In still other embodiments, the method employs partial drying of the collagen-drug solution in step (vi) and wherein the method further comprises applying a barrier layer comprising collagen derivatized by an acylation agent that imparts a barrier to diffusion of the drug to one side of the film, wafer, or membrane prior to ultraviolet radiation step (vii).

In this aspect as well, the invention also encompasses any collagen-based film or membrane prepared by the method described above.

In other aspects the invention includes methods of treating ophthalmic, otic, and sinus diseases by administering a collagen-based construct of the invention containing an ophthalmic, otic, or sinus drug, respectively. Accordingly, the invention also encompasses the use of any of the collagen-based constructs in methods of treating. In one particular aspect, a collagen-based construct comprising Latanoprost is used in a method of treating glaucoma comprising administering to the eye of a glaucoma patient a collagen-based, ultraviolet radiation crosslinked, film, wafer, or membrane delivery system comprising Latanoprost as described herein.

It is to be understood that both the foregoing general description and the following detailed description are exemplary and explanatory only and are not restrictive of the invention as claimed.

DETAILED DESCRIPTION OF THE INVENTION

The present application describes methods of preparing degradable collagen-based constructs that include therapeutic drugs or compounds and methods of using those constructs to deliver drug to a particular tissue or site, including optic, otic, and sinus tissues.

In one embodiment, the collagen-based constructs comprise a single drug reservoir alone with no rate controlling barrier. In another embodiment, the collagen-based constructs comprise at least one rate controlling barrier layer, said layers co-bonded to form a film construct such that the rate controlling barrier is located on one side of the construct to provide a barrier to drug diffusion in one direction and permit unidirectional delivery of said drug. In some examples, the drug reservoir layer and/or the rate controlling barrier layers have a thickness of from about 0.01 to about 1 mm, often from about 0.05 to about 0.5 mm, and in some cases from about 0.02 to about 0.2 mm.

The collagen-based constructs are designed to provide sustained release of drugs, including long-term and long-term release with zero order, or near zero order release kinetics. In some embodiments, the base collagen composition can be chemically derivatized to alter the overall ionic characteristics to better bind the drug component thereby altering the rate diffusion into tissues. Such constructs can be implanted to provide sustained and controlled release of therapeutic agents for ocular, otic, or sinus applications.

The implant site varies depending upon the indication. In some embodiments the implant site is submucosally. In other embodiments, the implant is transcleral, under a sclera flap, adjacent to the sclera, in the subjacent sclera near the macula, episcleral, subconjunctival, sub tenon, or in a fistula or fenestration, such as a fistula or fenestration created by surgery. Examples of implant sites are also provided in the Examples and throughout the Summary of the Invention and Detailed Description. In some embodiments, combinations of the sites are used.

Depending upon the embodiment, the constructs can be in the form of single layer films, wafers, or membranes, multilayer films, wafers, or membranes, unidirectional single layer films, wafers, or membranes, or unidirectional multilayer films, wafer, or membranes. In some embodiments, the film, wafer, or membrane constructs are composed of collagen that is chemically derivatized to alter the ionic properties to more efficiently bind specific agents or drugs to improve sustained delivery. Therapeutic agents or drugs are added to the films and membranes in quantities to provide uniform sustained, and in some embodiments, controlled, delivery for various therapeutic time intervals. In those embodiments involving unidirectional films or membranes, a physical or chemical barrier is applied to prevent diffusion of drugs and agents in one direction. In some embodiments, physical barriers are used in the form of an occlusive film bound to the base collagen construct. In other embodiments, chemical barriers are produced by chemically derivatizing one surface of the collagen constructs to create an occlusive barrier. The chemical barrier may be a hydrophobic surface to retard or prevent diffusion of hydrophilic drugs or agents and it may be hydrophilic surface to retard or prevent diffusion of hydrophobic agents or drugs.

Diffusion flux of therapeutic agents is dependent on ionic interactions between the collagen composition and the therapeutic agent, concentration of collagen composition and therapeutic agent, the aqueous solubility of the therapeutic agent, and diffusion barrier effectiveness. As described in more detail below, in some embodiments, the ionic properties of the collagen base may be altered by derivatizing collagen with agents that alter net charge to make the collagen more anionic or more cationic.

In some embodiments, the resorption rate of the collagen films and membranes is controlled by the degree of crosslinking accomplished by controlling the time of ultraviolet ("UV") irradiation.

In some embodiments, the collagen-based construct provides sustained release of a drug or other agent. "Sustained release" means release of a drug or other agent from a collagen-based film, membrane, wafer, or other construct for a period of time that is greater than one month. In some embodiments, the release is for greater than two months. In other embodiments, the release is for greater than about 3 months, 4 months, 5 months, 6 months, 7 months, 8 months, 9 months, 10 months, 11 months, or even 12 months. In some embodiments, the release is for greater than 6 months but for less than one year; for greater than 6 months but for less than 9 months; for greater than 6 months but for less than 8 months; or for greater than 6 months but for less than 7 months.

In one embodiment, the collagen-based construct provides controlled release of a drug or other agent. "Controlled release" means release of a drug or agent from a collagen-based film, membrane, wafer or other construct described herein that follows zero order, or nearly zero order, release for greater than one month, greater than 2 months, greater than about 3 months, about 4 months, 5 months, 6 months, 7 months, 8 months, 9 months, 10 months, 11 months, or even 12 months. In some embodiments, the release is for greater than 6 months but for less than one year; for greater than 6 months but for less than 9 months; for greater than 6 months but for less than 8 months; or for greater than 6 months but for less than 7 months. In some embodiments, controlled release includes an initial bolus release on day 1 or on about days 1 to 3. In other embodiments, the controlled release does not include a bolus release on day 1 so that zero order, or nearly zero order, release begins on day 1. In still other embodiments, the controlled release does not include a bolus release after day 3, so that zero order, or nearly zero order, release begins on about day 4. A controlled release is a sustained release, but a sustained release is not necessarily a controlled release.

In some embodiments, the collagen-based constructs provide sustained release and/or controlled release of a drug or other agent that is sparingly soluble in aqueous solution but soluble in alcohols and other water miscible solvents mixed into the collagen composition. Examples of such drugs and agents are provided below and in the Examples.

In one embodiment, the disclosure provides a method for preparing a collagen-based film, membrane, wafer or construct for sustained release of a therapeutic drug, comprising:
  (i) preparing derivatized collagen;
  (ii) dissolving the derivatized collagen precipitates in physiological buffer at concentrations ranging from 10 mg/mL to 100 mg/mL;
  (iii) adding active drug in a concentration that provides sustained release at therapeutic levels for at least 3 to 6 months;

(iv) optionally centrifuging the drug-containing, derivatized collagen to remove air bubbles;
(v) casting the collagen-drug solution into a thin layer or onto a mold;
(vi) drying or partially drying the solution to form a film, membrane, or wafer;
(vii) exposing the film, membrane, or wafer to ultraviolet ("UV") radiation in an oxygen-free atmosphere, such as a nitrogen atmosphere, for from about 17 to about 19 minutes; and
(viii) recovering the UV-crosslinked, drug-containing, film, membrane, or wafer.

In some embodiments, the concentration of the derivatized collagen in step (ii) is adjusted to a range between 15 mg/mL and 100 mg/mL, in other embodiments the concentration is adjusted to between about 25 mg/mL and about 60 mg/mL, while in still other embodiments, the concentration is adjusted to between about 30 mg/mL and about 45 mg/mL.

In some embodiments, the ultraviolet radiation exposure in step (vii) is for about 18 minutes.

In some embodiments, the UV-crosslinked film, membrane, or wafer is further treated by incubating it in a solution, for example a saline solution. In some embodiments, the solution treatment is for about 1 day, 2 days, 3 days, 4 days, 5 days, 6 days, 7, days, about 1 week, about 2 weeks, or about 3 weeks. The solution treatment helps to eliminate or reduce any initial bolus release of drug. For example, in some embodiments the solution treatment results in a film, membrane, or wafer that releases drug with zero order kinetics. In other embodiments, the solution treatment results in a film, membrane, or wafer that releases drug with near zero order kinetics. In still other embodiments, the solution treatment results in a film, membrane, or wafer that releases drug with an initial bolus until about day 1, day 2, or day 3, that is then followed by controlled release for at least about 3, 4, 5, 6, 7, 8, 9, 10, 11, or 12 months. In still further embodiments, the controlled release is for at least 6 months, but not for more than about 7, 8, 9, 10, 11, or 12 months.

In another embodiment, the method comprises preparing unidirectional collagen-based film constructs. In these embodiments, the drug reservoir layer is prepared generally as described above. However, following casting the solution into a thin layer and partial dehydration, a second barrier layer is applied to one side of the drug reservoir layer. The collagen composition for this layer is prepared by derivatizing collagen with an acylation agent that imparts a barrier to diffusion of the active agent. If the active agent is hydrophilic, the barrier layer should be hydrophobic. For example, soluble collagen can be derivatized with agents such as β-styrene sulfonyl chloride or polyvinyl sulfonic acid, ethylene/maleic anhydride copolymer or combinations of glutaric anhydride/β-styrene sulfonyl chloride, glutaric anhydride/polyvinyl sulfonic acid, glutaric anhydride/ethylene/maleic anhydride copolymer or other combinations of anhydrides, acid chlorides, sulfonyl chlorides, sulfonic acids producing hydrophilic derivatized collagen with anhydrides, acid chlorides, sulfonyl chlorides, or sulfonic acids producing hydrophobic derivatized collagens.

To prepare a unidirectional film, wafer, or membrane, a reservoir layer is prepared using purified, pepsin digested collagen derivatized with glutaric anhydride as previously described (U.S. Pat. Nos. 5,631,243 and 5,492,135). In general, the collagen solution is adjusted to pH 9.0 with 10 N and 1 N NaOH. While stirring the solution, glutaric anhydride is added at 10% (weight of collagen). The pH of the solution is then adjusted to 4.3 with 6 N and 1 N HCl to precipitate the derivatized collagen. The precipitate is centrifuged, washed in pyrogen-free deionized water, and then redissolved in phosphate buffer (0.01 M phosphate buffer, pH 7.4) to achieve a final concentration of approximately 30 mg/ml.

A barrier layer is prepared by derivatized purified collagen with glutaric anhydride and β-styrene sulfonyl chloride as previously described (U.S. Pat. No. 5,480,427). In general, the collagen solution is adjusted to pH 9.0 with 10 N and 1 N NaOH. While stirring the solution, glutaric anhydride is added at 10% (weight of collagen). For 5 minutes, the stirring is continued, and the pH maintained and 2% β-styrene sulfonyl chloride added at pH 9.0 and stirred. The pH of the solution is then adjusted to 4.3 to precipitate the derivatized collagen. The precipitate is centrifuged, washed one time, and then redissolved in phosphate buffer (0.01 M phosphate buffer, pH 7.4) to achieve a final concentration of approximately 30 mg/ml.

Uni-directional collagen films containing drug or agent is prepared by mixing the appropriate concentration of the drug or agent with glutaric anhydride-derivatized collagen (reservoir layer) described above. The mixture was centrifuged at 3500 rpm for 10 minutes if air bubbles are observed. The mixture is then poured into a mold and partially dried until it appears slightly gelatinous. A layer of barrier film collagen composition is the carefully placed on the surface of the reservoir layer and the molds placed again in the sterile laminar flow hood to fully dehydrate the unidirectional film. Release kinetics are adjusted as described for the non-unidirectional constructs. Films with a barrier layer are particularly useful for applications to the back of the eye so that the drug is effectively delivered in therapeutic levels to the target structures in the eye and not distributed to all surrounding tissues. The barrier containing films of this invention relate to collagen-based constructs or devices and methods for local drug delivery, and in particular directed to an implantable system intended to deliver therapeutic agents to a target tissue while limiting exposure to surrounding tissues and fluids while still achieving sustained drug levels, regionally or systemically.

Adjusting Ionic Characteristics of Base Collagen Compositions

Acylation reactions to derivatize soluble and insoluble collagen have been described by DeVore, et al. in a series of patents (U.S. Pat. Nos. 4,713,446, 4,851,513, 4,969,912, 5,067,961, 5,104,957, 5,201,764, 5,219,895, 5,332,809, 5,354,336, 5,476,515, 5,480,427, 5,631,243, and 6,161,544, each incorporated by reference). An increase in net negative charge density will increase ionic binding of agents with a net positive charge.

Specific acylation agents have been used to alter the net charge and charge density of intact tissue proteins. Certain agents can be used to change the net charge from positive to negative. These agents include, but are not limited to, anhydrides including maleic anhydride, succinic anhydride, glutaric anhydride, citractonic anhydride, methyl succinic anhydride, itaconic anhydride, methyl glutaric anhydride, dimethyl glutaric anhydride, phthalic anhydride, and many other such anhydrides. Acid chlorides include, but are not limited to, oxalyl chloride, malonyl chloride, and many others. Sulfonyl chlorides include, but are not limited to, chlorosulfonylacetyl chloride, chlorosulfonylbenzoic acid, 4-chloro-3-(chlorosulfonyl)-5-nitroebnzoic acid, 3-(chlorosulfonyl)-P-anisic acid, and others. Sulfonic acid include, but are not limited to, 3-sulfoebnzoic acid and others.

Certain agents can change the net charge from one positive to two negatives per reacted site. Specific agents include, but are not limited to, 3,5-dicarboxybenzenesulfonyl chloride and others.

Certain agents can be used to change the net charge from positive to neutral per reacted site. Specific agents include, but are not limited to, anhydrides including acetic anhydride, chloroacetic anhydride, propionic anhydride, butyric anhydride, isobutyric anhydride, isovaleric anhydride, hexanoic anhydride, and other anhydrides; acid chlorides including acetyl chloride, propionyl chloride, dichloropropionyl chloride, butyryl chloride, isobutyryl chloride, valeryl chloride, and others; sulfonyl chlorides including, but not limited to, ethane sulfonyl chloride, methane sulfonyl chloride, 1-butane sulfonyl chloride, and others.

Certain agents can be used to change the net charge from one positive to two positives per reacted site. Specific agents include, but are not limited to, 4,6-diamino-2-methylthiopyrimidine-5-sulfonic acid, and others.

Stability of Collagen Constructs

While the stability and durability of the different collagen drug delivery constructs can be assessed by monitoring drug release, other tests may also be used to measure their stability. For example, the robustness of the collagen constructs can be tested with trypsin or collagenase. For the trypsin digestion test, a collagen film, wafer, membrane, etc. is evaluated by incubating it without drug in 0.02% trypsin solution mixed in 1M Trizma buffer, pH 8.0 containing sodium chloride, calcium chloride and magnesium chloride. After 24 hours of incubation at 37° C., vials are centrifuged to recover the supernatant and analyzed for hydroxyproline using standard assays. The degradation profile is determined by calculating the hydroxyproline present in the incubation supernatant, which is indicative of collagen degraded as a result of trypsin digestion. A stable collagen construct should show negligible when incubated in trypsin.

For the collagenase test, a collagen film, wafer, membrane, etc. is incubated without drug in bacterial collagenase in sodium phosphate buffer, pH 7.4. After 24 hours of incubation at 37° C., vials are centrifuged to recover the supernatant and analyzed for hydroxyproline using standard assays. The degradation profile is determined by calculating the hydroxyproline present in the incubation supernatant, which is indicative of collagen degraded as a result of collagenase digestion. The degree of degradation is shown to be dependent on collagenase concentration.

Exemplary Drugs for Delivery

A variety of drugs are suitable for incorporation in the collagen constructs, consistent with their known dosages and uses. Thus, although certain examples are mentioned below and in the Examples section, those drugs are exemplary only. The inventors recognize that the collagen constructs provide a generalizable drug delivery system that can be used with many different therapeutic, or even diagnostic, agents or drugs.

As shown in the Examples, the collagen constructs described herein, including pretreated collagen constructs, provide sustained and zero order, or near zero order release of the drug Latanoprost (13,14-dihydro-17-phenyl-18,19,20-trinor-prostaglandin F2a-1-isopropyl ester). Latanoprost exhibits limited aqueous solubility (about 50 μg/mL in phosphate buffer) and is supplied in methyl acetate. It is readily miscible in ethanol and can be mixed in with soluble collagen. Thus, the results obtained with Latanoprost provide a specific example that provides evidence that other drugs and agents with low water or aqueous liquid solubility can also be incorporated into the collagen film/wafers described herein to provide delivery that is sustained (for example, 1, 2, 3, 4, 5, or 6 months or more) and/or controlled with either zero order or near zero order release.

A discussion of low water and aqueous solubility drugs for ophthalmic application is presented in US 2010/09008993 A1 (Proksch & Ward).

Examples of ophthalmic drugs with low water or aqueous liquid solubility included in the compositions of the present invention are selected from the group consisting of anti-inflammatory agents, anti-infective agents (including antibacterial, antifungal, antiviral, antiprotozoal agents), anti-allergic agents, antihistamines, antiproliferative agents, anti-angiogenic agents, anti-oxidants, antihypertensive agents, neuroprotective agents, cell receptor agonists, cell receptor antagonists, immunomodulating agents, immunosuppressive agents, intraocular ("IOP") lowering agents, carbonic anhydrase inhibitors, cholinesterase inhibitor miotics, prostaglandins and prostaglandin receptor agonists, prostaglandin F derivatives, prostaglandin $F_{2\alpha}$ receptor antagonists, cyclooxygenase-2 inhibitors, muscarinic agents, and combinations thereof.

Some non-limiting examples of ophthalmic drugs and their corresponding solubility in water are given in Table 1:

TABLE 1

Solubility of Ophthalmic Drugs

| Drug Name | Approx. Solubility in water (mg/mL) |
|---|---|
| NSAIDS | |
| indomethacin | 0.01 |
| piroxicam | 0.03 |
| ketoprofen | 0.11 |
| nepafenac | 0.02 |
| flurbiprofen | 0.008 |
| diclofenac | 0.0008 |
| etodolac | 0.016 |
| suprofen | 0.04 |
| naproxen | 0.016 |
| bromfenac | 0.013 |
| Immunosupressive Agents | |
| cyclosporin | 0.0095 |
| Steroids | |
| dexamethasone | 0.009 |
| betamethasone | 0.0005 |
| triamcinolone | 0.08 |
| loteprednol etabonate | 0.007 |
| Antiglaucoma | |
| epinephrine | 0.18 |
| dipivefrin | 0.058 |
| demecarium | 0.0001 |
| latanoprost | 0.052 |
| bimatoprost | 0.02 |
| travoprost | 0.008 |
| Antihistamine | |
| ketotifen | 0.008 |

Non-limiting examples of the glucocorticosteroids are: 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fiuprednidene acetate, fluprednisolone, flurandrenolide, fluticasone propionate, formocortal, halcinonide, halobetasol propionate, halometasone, halopredone acetate, hydrocortarnate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide, their physiologically acceptable salts, derivatives thereof, combinations thereof, and mixtures thereof. In one embodiment, the therapeutic agent is selected from the group consisting of difluprednate, loteprednol etabonate, prednisolone, combinations thereof, and mixtures thereof.

Non-limiting examples of the non-steroidal anti-inflammatory drugs ("NSAIDs") are: aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylacetic acid derivatives (e.g., aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (e.g., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (e.g., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (e.g., ampiroxicam, droxicam, isoxicam, lornoxicam, piroxicam, tenoxicam), .epsilon.-acetamidocaproic acid, S-(5'-adenosyl)-L-methionine, 3-amino-4-hydroxybutyric acid, amixetrine, bendazac, benzydamine, .alpha.-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, zileuton, their physiologically acceptable salts, combinations thereof, and mixtures thereof.

Non-limiting examples of antibiotics include doxorubicin; aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (e.g., azidamfenicol, chloramphenicol, florfenicol, thiamphenicol), ansamycins (e.g., rifamide, rifampin, rifamycin SV, rifapentine, rifaximin), .beta.-lactams (e.g., carbacephems (e.g., loracarbef)), carbapenems (e.g., biapenem, imipenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, cefbramide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefmetazole, cefminox, cefotetan, cefoxitin), monobactams (e.g., aztreonam, carumonam, tigemonam), oxacephems, flomoxef, moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin G benethamine, penicillin G benzathine, penicillin G benzhydrylamine, penicillin G calcium, penicillin G hydrabamine, penicillin G potassium, penicillin G procaine, penicillin N, penicillin O, penicillin V, penicillin V benzathine, penicillin V hydrabamine, penimepicycline, phenethicillin potassium, piperacillin, pivampicillin, propicillin, quinacillin, sulbenicillin, sultamicillin, talampicillin, temocillin, ticarcillin), lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin S, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin).

Other examples of antibiotics are the synthetic antibacterials, such as 2,4-diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofurantoin), quinolones and analogs (e.g., cinoxacin, ciprofloxacin, clinafloxacin, difloxacin, enoxacin, fleroxacin, flumequine, gatifloxacin, grepafloxacin, lomefloxacin, miloxacin, moxifloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (e.g., acetyl sulfamethoxypyrazine, benzylsulfamide, chloramine-B, chloramine-T, dichloramine T, $n^2$-formylsulfisomidine, $n^4$-.beta.-D-glucosylsulfanilamide, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidochrysoidine, sulfamoxole, sulfanilamide, 4-sulfanilamidosalicylic acid, n⁴-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (e.g., clofoctol, hexedine, methenamine, methenamine anhydromethylene citrate, methenamine hippurate, methenamine mandelate, methenamine sulfosalicylate, nitroxoline, taurolidine, xibomol).

Non-limiting examples of immunosuppressive agents include dexamethasone, cyclosporin A, azathioprine, brequinar, gusperimus, 6-mercaptopurine, mizoribine, rapamycin, tacrolimus (FK-506), folic acid analogs (e.g., denopterin, edatrexate, methotrexate, piritrexim, pteropterin, Tomudex®, trimetrexate), purine analogs (e.g., cladribine, fludarabine, 6-mercaptopurine, thiamiprine, thiaguanine), pyrimidine analogs (e.g., ancitabine, azacitidine, 6-azauridine, carmofur, cytarabine, doxifluridine, emitefur, enocitabine, floxuridine, fluorouracil, gemcitabine, tegafur), fluocinolone, triaminolone, anecortave acetate, fluorometholone, medrysone, and prednisolone.

Non-limiting examples of antifungal agents include polyenes (e.g., amphotericin B, candicidin, dermostatin, filipin, fungichromin, hachimycin, hamycin, lucensomycin, mepartricin, natamycin, nystatin, pecilocin, perimycin), azaserine, griseofulvin, oligomycins, neomycin undecylenate, pyirolnitrin, siccanin, tubercidin, viridin, allylamines (e.g., butenafine, naftifine, terbinafine), imidazoles (e.g., bifonazole, butoconazole, chlordantoin, chlormidazole, cloconazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole), acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, and zinc propionate.

Non-limiting examples of antiviral agents include acyclovir, carbovir, famciclovir, ganciclovir, penciclovir, and zidovudine.

Non-limiting examples of antiprotozoal agents include pentamidine isethionate, quinine, chloroquine, and mefloquine.

More broadly speaking, ophthalmic drugs include without limitation antibiotics, anti-fungals, anti-virals, anti-inflammatories, anti-glaucoma, anti-VEGF, and the like. Some specific examples of ophthalmic drugs include antibiotics such as tetracycline, chlortetracyline, bacitracin, neomycin, polymyxin, gramicidin, oxytetracycline, chloramphenicol, gentamycin, penicillin, kanamycin, amikacin, sisomicin, tobramycin, garamycin, ciprofloxacin, norfloxacin and erythromycin; antibacterials such as sulfonamides, sulfacetamide, sulfamethizole and sulfisoxazole; antivirals, including idoxuridine; and other antibacterial agents such as nitrofurazone and sodium propionate; anti-allergenics such as antazoline, methapyriline, chlorpheniramine, pyrilamin and prophenpyridamine; anti-inflammatories such as cortisone, hydrocortisone, hydrocortisone acetate, dexamethasone, dexamethasone 21-phosphate, fluocinolone, medrysone, prednisolone, methylprednisolone, prednisolone 21-phosphate, prednisolone acetate, fluorometholone, betamethasone, fluocortolone, indomethacin and triamcinolone; decongestants such as phenylephrine, naphazoline and tetrahydrazoline; miotics and anti-cholinesterase's such as pilocarpine, eserine salicylate, carbachol, di-isopropyl fluorophosphate, phospholine iodide, echothiophate, physostigmine and demecarium bromide; mydriatics such as atropine sulfate, cyclopentolate, homotropine, scopolamine, tropicamide, eucatropine, and hydroxyamphetamine; sympathomimetics such as epinephrine and immunosuppressants such as cyclosporin and azathioprine.

Exemplary drugs for glaucoma treatment include beta-blockers (e.g., timolol, betaxolol, levobetaxolol, carteolol, levobunolol, propranolol), carbonic anhydrase inhibitors (e.g., brinzolamide and dorzolamide), .alpha 1 antagonists (e.g., nipradolol), alpha 2 agonists (e.g. iopidine and brimonidine), miotics (e.g., pilocarpine and epinephrine), prostaglandin analogs (e.g., latanoprost (13,14-dihydro-17-phenyl-18, 19,20-trinor-prostaglandin F2a-1-isopropyl ester), travoprost, unoprostone, and compounds set forth in U.S. Pat. Nos. 5,889,052; 5,296,504; 5,422,368; and 5,151,444), "hypotensive lipids" (e.g., bimatoprost and compounds set forth in U.S. Pat. No. 5,352,708), and neuroprotectants (e.g., compounds from U.S. Pat. No. 4,690,931, particularly eliprodil and R-eliprodil, as set forth in a pending application U.S. Ser. No. 60/203,350 (PCT/US01/15074; PCT/US01/15169), and appropriate compounds from WO 94/13275, including memantine.

Exemplary therapeutic agents with low solubility in aqueous solution for otic applications may also include epinephrine, steroids, certain antibiotics as described above, and neurotrophins. Other exemplary drugs include, but are not limited to, Auralagan (benzocaine plus antipyrine), Ciprodex (ciprofloxacin and dexamethasone), Cortisporin (hydrocortisone, polymiyxin, and neosporin), Triethanolamine, and Ofloxacin (Floxin).

Exemplary therapeutic agents for sinus applications include, but are not limited to, (1) steroids selected from the group consisting of beclomethasone, flunisolide, fluticasone, triamcinolone, mometasone, aclometasone, desonide, hydro cortisone, betamethasone, clocortolone, desoximetasone, fluocinolone, flurandrenolide, mometasone, prednicarbate; amcinonide, desoximetasone, diflorasone, fluocinolone, fluocinonide, halcinonide, clobetasol, augmented betamethasone, diflorasone, halobetasol, prednisone, dexamethasone and methylprednisolone; (2) antimicrobials selected from the group consisting of: amantadine, amrimantadine, oseltamivir, zanamivir, inoglycosides, amikacin, tobramycin, amoxicillin, amoxicillin/clavulanate, amphotericin B, ampicillin, ampicillin/sulbactam, atovaquone, azithromycin, cefazolin, cefepime, cefotetan, cefpdoxime, ceftazidime, cefiriaxone, cefuroxime, cefhroxime axetil, chioramphenicol, clotrimazole, ciprofloxacin, clarithromycin, dapsone, doxycycline, erythromycin, fluconazole, foscarnet, ganciclovir, atifloxacin, imipenem/cilastatin, itraconazoic, ketoconazole, metronidazole, nystatin, penicillins including penicillin G, pentamidine, piperacillin/tazobactam, rifampin, quinupristin-dalfopristin, ticarcillin/clavulanate, trimethoprim/sulfamethoxazole, valacyclovir, mafenide, silver sulfadiazine, mupirocin, nystatin, triameinolone/nystatin, clotrimazole/betamethasone, clotrimazole, ketoconazole, butoconazole, miconazole, tioconazole, detergent-like chemicals that disrupt or disable microbes, menfegol, and N-docasanol, chemicals that block microbial attachment to target cells, chemicals that inhibits entry of infectious pathogens into cells, sulphated polymers, sulponated polymers, antiretroviral agents, agents which change the condition of the tissue to make it hostile to the microbes, agents which alter mucosal pH, buffer gel, acidform non-pathogenic microbes that kill or inhibit the growth of pathogenic microbes and antimicrobial metals.

Other exemplary agents include corticosteroid or other anti-inflammatory drugs as noted above (e.g., an NSAIDs), decongestants (e.g., vasoconstrictor), mucous thinning agents (e.g., an expectorant or mucolytic), agents that prevents or modifies an allergic response (e.g., an antihistamine, cytokine inhibitor, leucotriene inhibitor, IgE inhibitor, immunomodulator), anesthetic agents with or without a vasoconstriction agents (e.g. Xylocaine with or without Epinephrine), analgesic agents, hemostatic agents to stop bleeding, antiproliferative agents, cytotoxic agents e.g. stem cells, genes or gene therapy preparations, viral vectors carrying proteins or nucleic acids such as DNA or mRNA coding for important therapeutic functions or substances, cauterizing agents e.g. silver nitrate, etc.

In general, drugs are added to drug reservoir films or film layers at concentrations suitable to provide sustained release, and in some embodiments, controlled release, for appropriate therapeutic activity for desired delivery time periods. For example, as described in the Examples, Latanoprost (Xalatan®), a medication that reduces the pressure inside the eye, can be added as an ethanol solution to reconstituted, derivatized collagen solutions to produce a film construct providing at least a 3-month daily delivery of at least about 1.5 µg/day. Other examples are provided in the Detailed Disclosure and Examples.

Other drug reservoir films or film layers can similarly be prepared to provide delivery of therapeutically effective of amounts of each drug. In some embodiments, the delivery systems are prepared by forming films or membranes of acylated collagen containing extended therapeutic concentrations of selected drugs and exposing the drug containing compositions to ultraviolet irradiation in a nitrogen or other oxygen depleted atmosphere for time periods ranging from about 14 to about 19 minutes, about 15 to about 19 minute, about 16 to about 18 minutes, about 15, about 16, about 17, about 18, or about 19 minutes. In some embodiments, the exposure time is approximately 18 minutes.

Exposure to ultraviolet irradiation in a nitrogen (or other oxygen free) atmosphere is conducted to produce collagen films, wafers, or membranes with defined resorption characteristics ranging from greater than about 1 month, 2 months, 3 months, 4 months, 5 months, to about 6 months, or to greater than 6 months, the resorption characteristics being controlled by time of exposure to ultraviolet light in the oxygen free atmosphere. For example, exposure for about 18 minutes (or from 17 to 19 minutes) can be used to produce films or membranes resorbing or degrading after about 6 months. In some embodiments, the release is for greater than 6 months but for less than one year; for greater than 6 months but for less than 9 months; for greater than 6 months but for less than 8 months; or for greater than 6 months but for less than 7 months. Other exemplary release profiles for sustained and/or controlled release are described herein.

The present invention provides a number of advantages. For example, the present techniques and collagen film compositions facilitate an improved approach for sustained, and in some embodiments, controlled delivery of active agents where a precise dose and accurate placement are required. The dose can be adjusted to any desired amount, i.e., by modifying the concentration of compound in the film or the size of the film, and the solid nature of the film allows its placement at any site in the body which can be reached by surgical techniques. These features ensure that a delivered compound achieves a certain concentration at a specific site, reducing possible inaccuracy due to mistaken dose or improper placement.

Specific Ocular Pathology: Glaucoma

Glaucoma is a leading cause of blindness worldwide. While the exact etiology is unknown, there is either overproduction or impaired exit of aqueous humor from the eye causing elevated intraocular pressure (IOP). Elevated IOP causes damage to the optic nerve and, if untreated, can result in loss of vision.

There are many sub-types of glaucoma. The initial treatment is usually topical medication to lower the IOP by either reducing aqueous production or increasing aqueous outflow through the trabecular meshwork or uveal-scleral channels. Oral medication is also available but rarely used on a long term basis due to side effects. Surgery is performed when medical treatments do not control the IOP.

Ocular hypertension is a condition wherein intraocular pressure is elevated but no apparent loss of visual function has occurred; such patients are considered to be at significant risk for the eventual development of the visual loss associated with glaucoma. If ocular hypertension is detected early and treated promptly with medications that effectively reduce elevated intraocular pressure, loss of visual function or its progressive deterioration can generally be ameliorated.

Collagen-based drug delivery provides a simple and effective means of delivering pressure-lowering agents directly to the affected site to treat glaucoma and ocular hypertension.

Examples of agents used for treating glaucoma and ocular hypertension that can be delivered using the collagen-based constructs described herein include: beta-blockers (e.g., timolol, betaxolol, levobetaxolol, carteolol, levobunolol, propranolol); carbonic anhydrase inhibitors (e.g., dorzolamide); .alpha 1 antagonists (e.g.,); .alpha 2 agonists (e.g. iopidine and brimonidine), miotics (e.g., pilocarpine and phosphodiesterade inhibitors; sympathomimetics (e.g., epinephrine), prostaglandin analogs (e.g., travoprost, unoprostone, and compounds set forth in U.S. Pat. Nos. 5,889,052; 5,296,504; 5,422,368; and 5,151,444), "hypotensive lipids" (e.g., bimatoprost and compounds set forth in U.S. Pat. No. 5,352,708), and neuroprotectants (e.g., compounds from U.S. Pat. No. 4,690,931, particularly eliprodil and R-eliprodil, as set forth in U.S. Ser. No. 60/203,350 (PCT/US01/15074; PCT/US01/15169), and appropriate compounds from WO 94/13275, including memantine.

Under local or topical anesthesia, the collagen-based drug delivery construct containing a pressure lowering medication would be surgically implanted under the conjunctiva or tenon's capsule approximately 3 mm posterior to the limbus in between the rectus muscles. It would provide long term, zero order or near zero order drug delivery in a therapeutic amount but require essentially no patient involvement. Medication would be released and diffuse through the conjunctiva into the tear film constantly bathing the cornea and penetrating into the eye. In addition, an episcleral placement of the collagen-based drug delivery construct would be directly over the ciliary body, trabecular meshwork and Schlem's canal, which are the target sites for anti-glaucoma therapy. Thus, episcleral placement will also allow trans-scleral diffusion to these tissues, an advantage not found with topical medication. Accordingly, the drug delivery systems and constructs described herein provide methods of treating glaucoma and ocular hypertension.

Post Operative Drug Delivery

Another situation in which the collagen-based drug delivery constructs can be used is following surgery. Surgeons routinely prescribe medications after all types of surgery. For example, in almost every case, an ophthalmic surgeon will prescribe topical antibiotics as prophylaxis against infection. Topical corticosteroids and/or topical non-steroidal anti-inflammatory drugs (NSAID) are also routinely dispensed and are typically used at least four times per day. It is often difficult for patients to administer these medications during the post operative period due to tissue swelling, increased tearing and irritation. A passive drug delivery system, placed under the conjunctiva or tenon's capsule by the surgeon at the conclusion of the case, would eliminate the need for patients to administer drugs post-operatively. Thus, the drug delivery systems and constructs described herein provide methods of treating or preventing post-operative infection and other post-operative complications.

The subconjunctival fluids will cause the collagen in the device to hydrolyze thereby continuously releasing drugs in the sub-Tenon's or subconjunctival space. As the drugs are freed, they would diffuse through the conjunctiva and into the tear film constantly bathing the cornea and penetrating into the eye. Furthermore, since the device is placed on the episclera, some of the drugs will diffuse directly into the eye through the sclera; this is an advantage not found with topical application. After a predetermined time, the collagen delivery device will completely disappear.

Sinusitis Treatment

Collagen-based drug delivery constructs can also be used to deliver drugs directly into the sinuses, which are a frequent site of infection for the treatment of sinusitis. They are closed, difficult to access, and provide a very hospitable environment for organisms to thrive. More than 37 million Americans suffer from at least one episode of acute sinusitis each year. This represents approximately 1 of 7 Americans. The prevalence of sinusitis has soared in the last decade possibly due to increased pollution, urban sprawl, and increased resistance to antibiotics. For acute sinusitis, symptoms include facial pain/pressure, nasal obstruction, nasal discharge, diminished sense of smell, and cough not due to asthma (in children). Additionally, sufferers of this disorder can incur fever, fatigue, dental pain, and cough.

Sinusitis is an infection of the sinuses or inflammation of the sinuses. Infection is frequently a result of bacterial, viral or fungal etiologies. *Streptococcus pneumonia* is the most common cause of acute infections of the sinuses. When there is an infection, there is typically sinus pressure on both cheeks and heaviness in sinuses accompanied with chronic cough on occasion. In many patients, the chronic cough is a result of acute sinusitis. Sinusitis also presents with post nasal drip with a low grade fever and chills.

Other bacteria involved in acute sinusitis include *H. influenza* bacteria, which is more common in children under six years of age, and catarrhalis bacteria infection. Patients with nasal allergies can develop sinus infections due to a blockage of the opening of the sinuses into the nasal cavity. The ethmoid sinus, maxillary sinus and frontal sinus all drain into the nasal cavity. These become blocked as a result of the swelling of mucus membrane.

Sinus infections have very high recurrence rates. Another contributing factor to the severity of sinus infections is the fact that the sinuses afford an additional layer of protection to the harbored organisms, and they are thus very difficult to eradicate. Again these facts would indicate that a better means of targeting delivery would be more effective.

Short-term (acute) sinusitis usually lasts less than 4 weeks. Up to two-thirds of people with acute sinusitis improve without antibiotic treatment. Sinus infections are commonly caused by viral infections, which do not respond to antibiotics. Most people recover fully when treated with an antibiotic for acute sinusitis that is caused by a bacterial infection.

Sinusitis that lasts 8 weeks or longer is called chronic sinusitis. It is more difficult to treat and responds more slowly to antibiotics than acute sinusitis. Antibiotic therapy is usually recommended for chronic sinusitis and may require a longer course of treatment and multiple antibiotics. A corticosteroid that reduces inflammation and swelling of the lining of the nasal passages may also be used during treatment.

In some people, a sinus infection may be caused by a fungus or a bacterium other than those normally associated with sinusitis. People who have an impaired immune system are at risk for these unusual infections. It also may include people who must use oral or inhaled corticosteroid medications. Fungal sinusitis, which accounts for a significant number of chronic sinusitis cases, does not respond to antibiotic treatment and may need treatment with antifungal medications, corticosteroids, or surgery.

Surgery may be required upon failure of antibiotics for an extended period of time. Symptoms of chronic sinusitis are often vague and may not respond well to treatment. It may take time and patience to find a successful treatment. Thus, a durable treatment modality would serve this patient population exceedingly well.

Oral antibiotics are one of the most prescribed treatments for chronic sinusitis patients. For this treatment, doctors prescribe a number of broad-spectrum antibiotics that a patient takes daily for approximately 2-3 weeks.

Nebulized antibiotics are a means of treating infections topically. This treatment consists of breathing in the antibiotics through the nose, which allows the antibiotics to get directly to the source of the problem. In select cases, intravenous antibiotic therapy is the method of choice.

Some currently utilized agents are: Antibiotics, such as Amoxil (Amoxacillin), Augmentin (amoxacillin-clavulate), Avelox (Moxifloxacin HCl), Bactrim (Sulfamethoxazole-Trimethoprim), Biaxin (clarithryomycin), Cipro (ciprofloxacin), Avelox (moxifloxacin), Doxycycline, Levaquin (levofloxacin), Tequin (gatifloxacin), Zithromax (azithromycin); Decongestents, such as, Claritin (loratadine), Clarinex (desloratadine), Allegra (fexofenadine), Zyrtec (cetirizine HCL), Chlor-Trimeton (chiorpheneramine maleate); and other drugs, such as corticosteroids, antihistamines, or pseudoephedrine.

Sinus surgery is generally a last line of defense for doctors to relieve a chronic sinusitis condition. Most surgeries are endoscopic surgeries, which allows the surgeon to operate without making facial incisions. The surgery is generally accomplished in one to three hours, and can take several weeks for a full recovery.

A durable mechanism of drug delivery to the sinuses would be a welcome addition to the armamentarium of the treating physicians. A pharmaceutical agent, when afforded a longer resident time in this hostile environment, would have a greater opportunity to successfully eradicate the organisms as well as prevent any disease recurrence. Thus, collagen-based drug delivery constructs in conjunction with the appropriate antibiotics, antiviral agents, anti-fungal agents, anti-inflammatory agents, and other remedies will provide a very effective means for preferential treatment of bacterial, fungal, and viral sinus infections.

The constructs can be directly inserted into one or more of a naturally occurring or man-made anatomical cavity or passageway such as a nostril nasal cavity, meatus, interior of sinus, etc. to deliver a therapeutic substance to tissues located adjacent to or near the implanted device As with constructs prepared for optic use, constructs for sinus use are prepared by adding drugs to drug reservoir films or film layers at concentrations suitable to provide sustained release, and in some embodiments, controlled release, for appropriate therapeutic activity for desired delivery time periods. In some embodiments, the delivery systems are prepared by forming films or membranes of acylated collagen containing extended therapeutic concentrations of selected drugs and exposing the drug containing compositions to ultraviolet irradiation in a nitrogen (or other oxygen free) atmosphere for time periods ranging from about 14 to about 19 minutes, about 15 to about 19 minutes, about 16 to about 18 minutes, about 15, about 16, about 17, about 18, or about 19 minutes. In some embodiments, the exposure time is approximately 18 minutes. Exposure to ultraviolet irradiation in a nitrogen (or other low oxygen) atmosphere is conducted to produce collagen films or membranes with defined resorption characteristics as described herein, for example, ranging from greater than about 1 month, 2 months, 3 months, 4 months, 5 months, to about 6 months, the resorption characteristics being controlled by time of exposure to ultraviolet light in an oxygen free atmosphere.

Otitis Media Therapy

Another application for collagen-based drug delivery constructs is in drug delivery into the middle ear for the treatment of otitis media. The middle ear is has some of the same resistant characteristics as the sinuses. Otitis media is an inflammation and/or infection of the middle ear. Acute otitis media (acute ear infection) occurs when there is bacterial or viral infection of the fluid of the middle ear, which causes production of fluid or infection. Chronic otitis media occurs when the eustachian tube becomes blocked repeatedly due to allergies, multiple infections, ear trauma, or swelling of the adenoids.

Otitis media is the second most common disease of childhood, after upper respiratory infection. It is also the most common cause for childhood visits to a physician's office, accounting for approximately 20 million annual physician visits. Various epidemiologic studies report the prevalence rate of acute Otitis media to be 17-20% within the first 2 years of life, and 90% of children have at least one documented middle ear effusion by age 2 years. Acute Otitis media is a recurrent disease. More than one third of children experience 6 or more episodes of acute Otitis media by age 7 years.

Chronic suppurative Otitis media is a chronic inflammation of the middle ear that persists at least 6 weeks and is associated with otorrhea through a perforated TM, an indwelling tympanostomy tube or a surgical myringotomy. Morbidity from this disease remains significant, despite frequent use of systemic antibiotics to treat the illness and its complications. Intratemporal and intracranial complications of otitis media are the 2 major types. Intratemporal complications include hearing loss (conductive and sensorineural), tympanic Membrane perforation (acute and chronic), chronic suppurative otitis media (with or without cholesteatoma), cholesteatoma, tympanosclerosis, mastoiditis, petrositis, labyrinthitis, facial paralysis, cholesterol granuloma, and infectious eczematoid dermatitis. Intracranial complications include meningitis, subdural empyema, brain abscess, extradural abscess, lateral sinus thrombosis, and otitic hydrocephalus.

Compliance, duration of therapy, and cost are important issues in treating children with acute otitis media. The primary determinants of compliance appear to be frequency of dosing, palatability of the agent, and duration of therapy. Less frequent doses are more desirable than more frequent doses, which interfere with daily routines. Shorter duration of therapy increases compliance but should be used only when equal clinical efficacy can be assured. In many instances, palatability ultimately determines compliance in children.

Most cases of otitis media externa occur after an episode of acute otitis media, and 67% of patients develop a middle ear effusion. The mean duration of the effusions is 23 days, but many persist much longer. Most cases of chronic otitis media are associated with conductive hearing loss, averaging approximately 25 dB. The following are among the many strategies advocated for medical treatment in patients with Otitis media externa: antimicrobials; antihistamine-decongestants, intranasal and systemic steroids, nonsteroidal anti-inflammatory drugs (NSAIDs), mucolytics, and aggressive management of allergic symptoms.

Controversy continues over the optimal management of Otitis media. The current therapeutic regimens of tubes and antibiotics seem very inadequate in many cases. Clearly a more durable treatment would be optimal so that here, too, a collagen-based drug delivery construct would afford patients a much more effective and durable treatment. The construct can be inserted through a preexisting opening that was utilized for the placement of tubes. Inner ear tissue structures that may be targeted for treatment purposes include but are not limited to the cochlea, the endolymphatic sac/duct, the vestibular labyrinth, and all of the compartments (and connecting tubes) which include these components. Access to these and other inner ear tissue regions is typically achieved through a variety of structures, including but not limited to the round window membrane, the oval window/stapes footplate, the annular ligament, and the otic capsule/temporal bone, all of which are considered "middle-inner ear interface tissue structures." Furthermore, as used herein, "middle ear" means the physiological air-containing tissue zone behind the tympanic membrane (e.g. the ear drum) and ahead of the inner ear.

Once again, the construct will have a protracted resident time in the middle ear, and thereby will be more durable. This durability will provide a more effective treatment against the pathological organisms, as well as decrease the possibility of recurrent disease because of its ability to more completely eradicate the pathological organisms.

As with constructs prepared for optic or sinus use, constructs for otic use are prepared by adding drugs to drug reservoir films or film layers at concentrations suitable to provide sustained release, and in some embodiments, controlled release, for appropriate therapeutic activity for desired delivery time periods. In some embodiments, the delivery systems are prepared by forming films or membranes of acylated collagen containing extended therapeutic concentrations of selected drugs and exposing the drug containing compositions to ultraviolet irradiation in a nitrogen atmosphere for time periods ranging from about 14 to about 19 minutes, about 15 to about 19 minutes, about 16 to about 18 minutes, about 15, about 16, about 17, about 18, or about 19 minutes. In some embodiments, the exposure time is approximately 18 minutes. Exposure to ultraviolet irradiation in a nitrogen (or other oxygen free) atmosphere is conducted to produce collagen films or membranes with defined resorption characteristics as described herein, for example, ranging from greater than about 1 month, 2 months, 3 months, 4 months, 5 months, to about 6 months, or to greater than 6 months, the resorption characteristics being controlled, at least in part, by time of exposure to ultraviolet light in a nitrogen atmosphere.

The features and other details of the invention will now be more particularly described and pointed out in the following examples describing preferred techniques and experimental results. These examples are provided for the purpose of illustrating the invention and should not be construed as limiting, particularly with respect to the exemplified drug.

EXAMPLES

Example 1

Sustained Release from Multi-directional Collagen-based Films

Preparation of Collagen

Purified, pepsin digested collagen at 3 mg/mL was obtained from Advanced Biomatrix, Inc. and derivatized with glutaric anhydride as previously described (U.S. Pat. Nos. 5,631,243 and 5,492,135, incorporated by reference). Briefly, the collagen solution was adjusted to pH 9.0 with 10 N and 1 N NaOH. While stirring the solution, glutaric anhydride was added at 10% (weight of collagen). For 5 minutes, the stirring continued, and the pH was maintained.

The pH of the solution was then adjusted to 4.3 with 6 N and 1 N HCl to precipitate the derivatized collagen. The precipitate was centrifuged at 3500 rpm for 20 minutes and washed one time in pyrogen-free deionized water and then redissolved in phosphate buffer (0.01 M phosphate buffer, pH 7.4) to achieve a final concentration of approximately 30 mg/ml.

Preparation of Collagen Delivery Systems Containing Latanoprost

To prepare Latanoprost (13,14-dihydro-17-phenyl-18,19,20-trinor-prostaglandin F2a-1-isopropyl ester) collagen films or wafers, 50 µL of Latanoprost in ethanol at 50 µg/µL was mixed with 1 mL of derivatized collagen described above. The mixture was centrifuged at 3500 rpm for 10 minutes if air bubbles were observed. 100 µL aliquots of the mixture containing 250 µg of Latanoprost were then syringed onto 8 mm diameter polypropylene molds. The molds were placed in a laminar flow hood until the concentrated collagen plus Latanoprost was dry.

A. Polymerized Collagen Films/Wafers

The dried collagen films or wafers were placed in a controlled atmosphere chamber containing an ultraviolet lamp emitting 254 nm of irradiation. Prior to activating the ultraviolet lamp, the chamber was flushed with nitrogen gas. After 5 minutes of flushing, the exit port was closed, the ultraviolet lamp activated and the collagen composition exposed to 254 nm ultraviolet irradiation for 14-18 minutes while continuing to flush the chamber to maintain chamber expansion. The resulting materials are referred to herein as "polymerized films/wafers."

B. "Pretreated Collagen Films/Wafers"

Another set of film/wafers were prepared as described above. In this case, however, the polymerized films/wafers containing 250 µg of Latanoprost per wafer were pretreated in 0.1M phosphate buffer for 7 days to permit initial bolus release of drug prior to use in experiments. The preparations are referred to as the "pretreated films/wafers".

C. In Situ Polymerizing Collagen Gels

In situ polymerizing collagen gels was prepared by extensive dialysis of salt precipitated collagen against 0.035 M EDTA with step-wise increase of pH to 7.5. Latanoprost was dissolved in ethanol and added to polymerizing collagen gels to provide gel depots containing 250 µg of Latanoprost/100 µL collagen gel.

Evaluation of Latanoprost Release In Vitro

In the first experiment, collagen gels containing Latanoprost were incubated in 1.0 mL of physiologic saline at 37° C. The entire 1.0 mL volume was removed at time periods ranging from 1 day to 27 days and replaced with 1.0 mL of fresh buffer. Latanoprost concentration in buffer aliquots was measured by HPLC analysis (Millennium Research Laboratories). Detection at nanogram levels was validated using Latanoprost standards and concentration curves generated.

In the second experiment, four 8 mm diameter polymerized films/wafers were placed in 1.5 mL vials containing 1 mL of 0.1 M phosphate buffer, pH 7.4. The vials were placed in a controlled temperature chamber at 37° C. Two of the films/wafers were exposed to UV irradiation for 14 minutes. The second set of films/wafers were exposed to UV irradiation for 18 minutes. At various time intervals from day 1 to day 180 the entire 1.0 mL of buffer was removed from the vials and replaced with fresh buffer. Collected buffer solution was then assayed for Latanoprost using an EIA kit (Cayman Chemical). Buffer has continued to be removed from the 18 minute UV exposed Latanoprost samples out to more than 240 days. The second set of films/wafers exposed to UV irradiation for 14 minutes began to degrade after 180 days. Initial results are presented below. Additional assay results for Latanoprost concentration is pending.

In a third experiment, three pretreated 8 mm diameter polymerized films/wafers containing 250 µg of Latanoprost per wafer were placed in 1.5 mL vials containing 1 mL of 0.1 M phosphate buffer, pH 7.4. The vials were placed in a controlled temperature chamber at 37° C. At various time intervals from day 1 (after pretreatment) to day 70, the entire 1.0 mL of buffer was removed from the vials and replaced with fresh buffer. Collected buffer solution was then assayed for Latanoprost using an EIA kit (Cayman Chemical). Buffer has continued to be removed from the Latanoprost samples out to more than 140 days. Initial assay results are presented below. Additional assay results of Latanoprost release from day 70 to day 148 for the pretreated films/wafers is pending.

Figure 1:
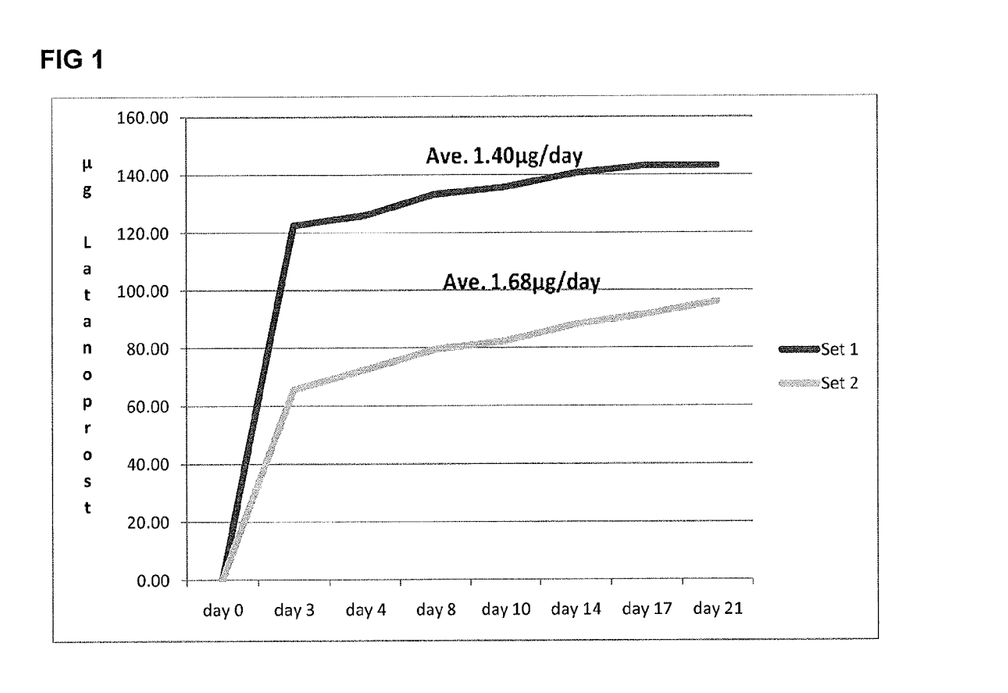
FIG. 1 depicts the release of Latanoprost from in situ polymerizing collagen gels, as measured by HPLC.

Both in situ polymerizing collagen gels and solid collagen films/wafers produced sustained release of Latanoprost. HPLC analysis of release from the polymerizing gels showed a large initial release of Latanoprost from polymerizing gels added directly to buffer solution followed by sustained release averaging 1.4 µg/day. (FIG. 1, set 1.) Polymerizing gels partially pre-polymerized before placing in buffer solution showed reduced initial release followed by sustained release averaging 1.68 µg/day. (FIG. 1, set 2.) Release from gels was near steady state following a large bolus release of up to day 3. (FIG. 1).

Figure 2:
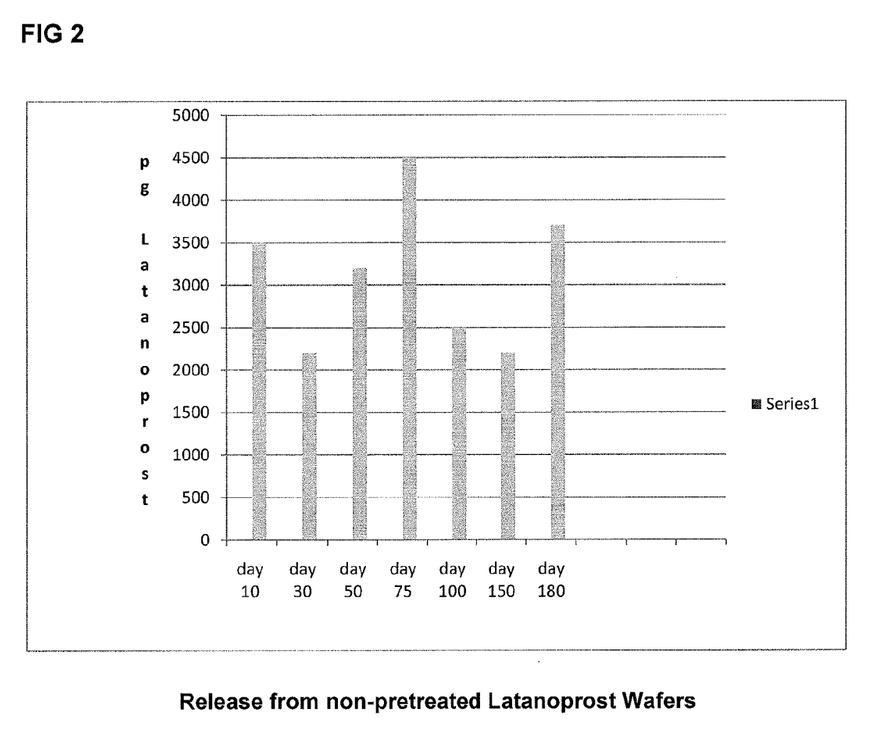
FIG. 2 depicts the release of Latanoprost from collagen wafers/films as measured by EIA.
Figure 3:
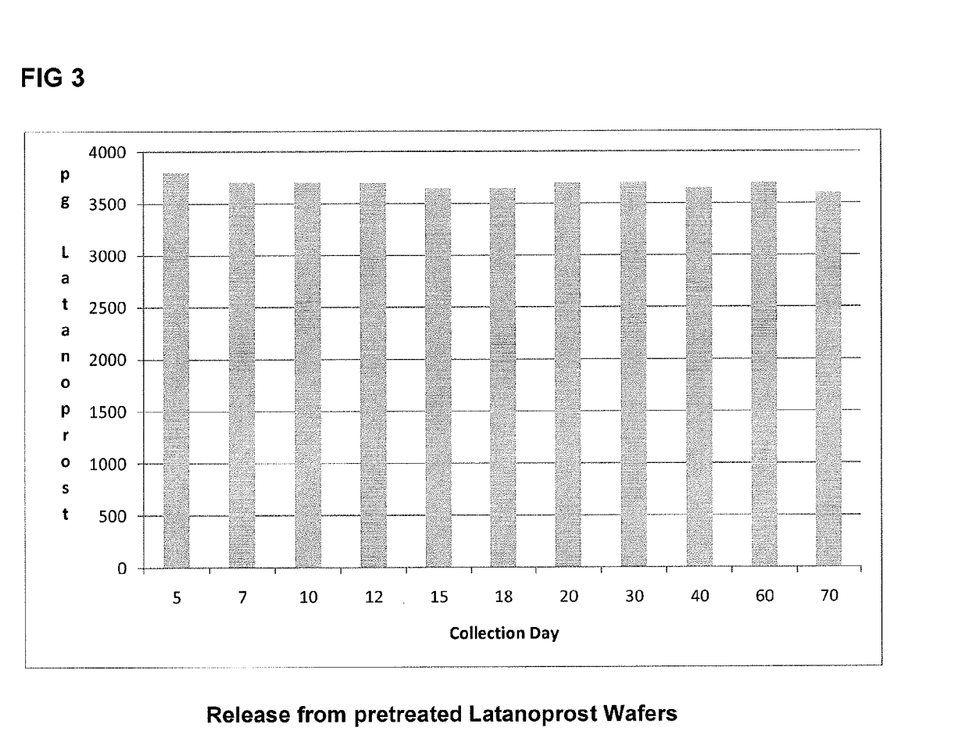
FIG. 3 depicts the release of Latanoprost from collagen wafers/films pre-treated in buffer.

Release from UV polymerized films/wafers was measured using the Latanoprost EIA kit from Cayman Chemical Company following kit instructions out to 180 days. (FIG. 2.) The pretreated UV polymerized films/wafers (pre-treated in buffer for 7-10 days) had a nearly steady state release for the 70 days measured following pretreatment. (FIG. 3.)

Degradation of Collagen Films/Wafers

During in vitro incubation in buffer solution, the in situ polymerizing collagen gels remained present throughout the 27-day testing period and beyond. In vitro incubation of collagen films/wafers containing Latanoprost remained intact throughout the testing period noted above. Films/wafers exposed to UV irradiation for 14 minutes began to degrade after 180 days. Films/wafers exposed to UV irradiation for 18 minutes appeared intact even after 248 days. Pretreated films/wafers appeared intact after 145 days of incubation.

Therapeutic Potential of Latanoprost Released from Collagen Films

Results of Latanoprost release experiments demonstrate the potential of providing a durable implant for sustained release of Latanoprost for effective treatment of glaucoma. Although both in situ polymerizing collagen gels and the collagen wafers/films could be used in the treatment of glaucoma if such collagen depots were injected (gel) or implanted (wafer) in, for example, the subconjunctival space, the pre-treated wafers provided a sustained release without the initial burst observed with the polymerizing gel. Based on the sustained release observed through day 180, it is anticipated that the collagen wafers can be used to deliver Latanoprost for a period of at least 6 months following each implantation, and even longer delivery periods may be feasible.

Pharmacokinetic Study in Rabbits

A Stage 1 PK study was conducted in the rabbit model. Six animals were included in this preliminary PK study. Collagen films/wafers were fabricated as described above and cut into circular shapes of approximately 5 mm or oval shapes approximately 4 mm wide by 3 mm long. Latanoprost wafers were loaded with either 100 µg of Latanoprost/wafer or 200 µg of Latanoprost/wafer. The conjunctival tissue was prepared for wafer insertion by exposing the superior-temporal bulbar conjunctival area in an area approximately 1 mm away from the corneal limbus and dissecting the conjunctiva with scissors under a surgical microscope. Wafers were placed into the conjunctival incision. In some cases the wafers were trimmed before insertion. Seven days following wafer insertion, wafers were removed and the following tissues and fluids were removed for testing: aqueous fluid, vitreous, iris/ciliary tissue, and inferior and posterior conjunctival tissue. Aqueous samples were assayed for Latanoprost acid using the EIA kit from Cayman Chemical Company. Latanoprost acid was detected in all rabbit aqueous samples. However, results were complicated by possible interference from endogenous IgG and IgE antibodies in the rabbit aqueous. Final results are pending.

Example 2

Sustained Release from Uni-directional Collagen-based Films

Reservoir Layer:

Purified, pepsin digested collagen at 3 mg/mL is obtained from Advanced Biomatrix, Inc. and derivatized with glutaric anhydride as previously described (U.S. Pat. Nos. 5,631,243 and 5,492,135). Briefly, the collagen solution is adjusted to pH 9.0 with 10 N and 1 N NaOH. While stirring the solution, glutaric anhydride is added at 10% (weight of collagen). For 5 minutes, the stirring is continued, and the pH maintained. The pH of the solution is then adjusted to 4.3 with 6 N and 1 N HCl to precipitate the derivatized collagen. The precipitate is centrifuged at 3500 rpm for 20 minutes and washed one time in pyrogen-free deionized water and then redissolved in phosphate buffer (0.01 M phosphate buffer, pH 7.4) to achieve a final concentration of approximately 30 mg/ml.

Barrier Layer:

Purified, pepsin digested collagen at 3 mg/mL is obtained from Advanced Biomatrix, Inc. and derivatized with glutaric anhydride and β-styrene sulfonyl chloride as previously described (U.S. Pat. No. 5,480,427). Briefly, the collagen solution is adjusted to pH 9.0 with 10 N and 1 N NaOH. While stirring the solution, glutaric anhydride is added at 10% (weight of collagen). For 5 minutes, the stirring is continued, and the pH maintained and 2% β-styrene sulfonyl chloride added at pH 9.0 and stirred for another 10 minutes. The pH of the solution is then adjusted to 4.3 with 6 N and 1 N HCl to precipitate the derivatized collagen. The precipitate is centrifuged at 3500 rpm for 20 minutes, washed one time in pyrogen-free deionized water and then redissolved in phosphate buffer (0.01 M phosphate buffer, pH 7.4) to achieve a final concentration of approximately 30 mg/ml.

Preparation of Uni-directional Collagen Films Containing Latanoprost

To prepare Latanoprost uni-directional collagen films, 50 µg of Latanoprost ethanol solution containing 50 µg/µL is mixed with 1 mL of glutaric anhydride-derivatized collagen (reservoir layer) described above. The mixture is centrifuged at 3500 rpm for 10 minutes if air bubbles were observed. Aliquots of 100 µL are syringes onto 8 mm diameter polypropylene molds or onto plates. The molds/plates are placed in a laminar flow hood until the collagen plus Latanoprost is partially dried, appearing slightly gelatinous. A layer of barrier film collagen composition is carefully placed on the surface of the reservoir layer and the wells placed again in the sterile laminar flow hood to fully dehydrate the unidirectional film.

The dried collagen film is placed in a controlled atmosphere chamber containing an ultraviolet lamp emitting 254 nm of irradiation. Prior to activating the ultraviolet lamp, the chamber is flushed with nitrogen gas or otherwise rendered oxygen free. After 5 minutes of flushing, the exit port is closed, the ultraviolet lamp activated and the collagen composition exposed to 254 nm ultraviolet irradiation for 18 minutes while continuing to flush the chamber to maintain chamber expansion.

Planned Evaluation of Latanoprost Diffusion Though Barrier Layer

Polymerized films are cut to tightly fit on the filter of 2 mL, nonsterile, 0.45 µm Nylon Membrane, Centrifugal Filter Tubes. Buffer is placed on the reservoir side of the film and placed in a 37° C. incubator for 1 hour, 6 hours, 24 hours, and 48 hours. Aliquots of the buffer passing through the film/filter are analyzed for Latanoprost. Control films without barrier film are also tested. Latanoprost concentration is measured as described in Experiment 1. It is anticipated that the diffusion experiments will demonstrate the effectiveness of the barrier layer in preventing Latanoprost diffusion through the barrier layer, thus providing uni-directional films to enhance the effectiveness of drug release.

Although the present invention has been described with reference to exemplary embodiments, one skilled in the art can easily ascertain its essential characteristics and without departing from the spirit and scope thereof, can make various changes and modifications of the invention to adapt it to various usages and conditions. Those skilled in the art will recognize or be able to ascertain using no more than routine experimentation, many equivalents to the specific embodiments of the invention herein. Such equivalents are intended to be encompassed in the scope of the present invention.

All references, including patents, publications, and patent applications, mentioned in this specification are herein incorporated by reference in the same extent as if each independent publication, patent or patent application was specifically and individually indicated to be incorporated by reference.

We claim:

1. A collagen-based, ultraviolet radiation crosslinked, film, wafer, or membrane construct comprising at least one layer of chemically derivatized collagen and an amount of an ophthalmic, otic, or nasal drug that has low water or aqueous solubility, wherein the amount of the drug is sufficient to provide a therapeutically effective amount of drug per day over a period of at least three months, and further wherein the construct has been exposed to ultraviolet radiation crosslinking for a period of 17 to 19 minutes in a low oxygen environment.

2. The collagen-based film, wafer, or membrane of claim 1, wherein the drug present in the film, wafer, or membrane is resistant to removal by a 1 day treatment in an aqueous buffer.

3. The collagen-based film, wafer, or membrane of claim 2, wherein the drug present in the film, wafer, or membrane is resistant to removal by a 7 day treatment in an aqueous buffer.

4. The film, wafer, or membrane of any one of claims 1 to 3, further comprising a barrier layer of collagen derivatized by an acylation agent.

5. A collagen-based, ultraviolet radiation crosslinked, film, wafer, or membrane delivery system comprising at least one layer of glutaric anhydride derivatized collagen and at least about 150 μg of Latanoprost, wherein the film, wafer, or membrane has been crosslinked with ultraviolet radiation for from 17 to 19 minutes.

6. The collagen-based film, wafer, or membrane of claim 5, wherein the film, wafer, or membrane provides sustained and/or controlled release of about 1.5 μg Latanoprost per day for at least about 6 months but for less than one year.

7. The film, wafer, or membrane delivery system of claim 5, wherein the film, wafer, or membrane comprises at least about 300 μg Latanoprost to provide an effective dosage of about 1.5 μg per day for at least about 180 days of sustained and/or controlled delivery.

8. The collagen-based film, wafer, or membrane of claim 5, wherein the Latanoprost present in the film, wafer, or membrane is resistant to removal by a 1 day treatment in an aqueous buffer.

9. The collagen-based film, wafer, or membrane of claim 8, wherein the Latanoprost present in the film, wafer, or membrane is resistant to removal by a 7 day treatment in an aqueous buffer.

10. The film, wafer, or membrane of any one of claims 5 to 9, further comprising a barrier layer of collagen derivatized by an acylation agent.

11. A method for preparing a collagen-based film, wafer, or membrane construct comprising a therapeutic drug and capable of providing sustained and/or controlled release of that drug, the method comprising:
(i) preparing derivatized collagen;
(ii) dissolving the derivatized collagen precipitates in physiological buffer at concentrations ranging from 10 mg/mL to 100 mg/mL;
(iii) adding active drug in an amount and concentration sufficient to provide sustained release at therapeutic levels for at least three months;
(iv) casting the collagen-drug solution into a thin layer or onto a mold;
(v) drying or partially drying the solution to form a film, membrane, or wafer;
(vi) exposing the film, membrane, or wafer to ultraviolet ("UV") radiation in a low oxygen atmosphere for from about 17 to about 19 minutes; and
(vii) recovering the UV-crosslinked, drug-containing, film, membrane, or wafer, wherein the film, membrane, or wafer is able to provide sustained release of the active drug at therapeutic levels for at least three months.

12. The method of claim 11, wherein the ultraviolet radiation exposure in step (vii) is for about 18 minutes.

13. The method of claim 11, wherein the method further comprises treating the UV-crosslinked collagen construct an aqueous solution for about 1, 2, 3, 4, 5, 6, or 7 days.

14. The method of claim 11, wherein the drug is Latanoprost in an amount sufficient to release an effective dosage of about 1.5 μg per day for at least about 180 days.

15. The method of claim 11, wherein the method employs partial drying of the collagen-drug solution in step (vi) and wherein the method further comprises applying a barrier layer comprising collagen derivatized by an acylation agent that imparts a barrier to diffusion of the drug to one side of the film, wafer, or membrane prior to ultraviolet radiation step (vii).

16. A collagen-based film or membrane prepared by the method of any one of claims 11 to 15.

17. A method of treating glaucoma comprising administering to the eye of a glaucoma patient the collagen-based, ultraviolet radiation crosslinked, film, wafer, or membrane delivery system comprising Latanoprost of any one of claims 5 to 10.

* * * * *